United States Patent [19]

Masuda

[11] Patent Number: 5,183,477
[45] Date of Patent: Feb. 2, 1993

[54] FOLIAR SPRAY AGENT FOR PROTECTING AGRICULTURAL AND HORTICULTURAL PLANTS AGAINST DISEASE INJURY

[76] Inventor: Toshio Masuda, 37-12, Bessho-machi, Ohmiya-shi, Saitama-ken, Japan

[21] Appl. No.: 102,011

[22] Filed: Oct. 24, 1990

[30] Foreign Application Priority Data

Oct. 26, 1989 [JP] Japan .................................. 1-277124

[51] Int. Cl.$^5$ ............................................. A01C 1/00
[52] U.S. Cl. ......................................... 47/58; 47/1.01; 71/62; 71/64.1
[58] Field of Search ....................... 71/62; 47/58, 1.01

[56] References Cited

PUBLICATIONS

CA101(15):129623p Khoroshkin, "Leaf . . . silicon" 1983.
CA99(17):138771c Khoroshkin et al., "Cultivation . . . barley" 1982.
CA76(19):109144v Yates "Effects . . . gibberellin" 1972.

Primary Examiner—Ferris Lander
Attorney, Agent, or Firm—Pennie & Edmonds

[57] ABSTRACT

A foliar spray agent containing an alkali metal silicate as an active ingredient protects agricultural and horticultural plants from disease injury by spraying on the leaves of plants. Treatment of agricultural and horticultural plants with the agent provides an increase in crop yields with high quality.

3 Claims, No Drawings

FOLIAR SPRAY AGENT FOR PROTECTING AGRICULTURAL AND HORTICULTURAL PLANTS AGAINST DISEASE INJURY

FIELD OF THE INVENTION

The present invention relates to a foliar spray agent for protecting agricultural and horticultural plants from disease injury which comprises a alkali metal silicate as an active ingredient, and a method of protecting agricultural and horticultural plants against disease injury using said agent.

The agent of the invention protects various agricultural and horticultural plants effectively from disease injury by using a natural ingredient harmless to human and animals, without any crop contamination usually caused by conventional synthetic organic pesticides, and provides a striking increase in crop yield.

BACKGROUND OF THE INVENTION

There has been described (Eiichi Takahashi, "Silicic acid plant and lime plant—investigating properties of the plants" published by incorporated cultural association of agricultural, industrial and fishing village) an attempt to increase the yield of rice by adding approximately 100 ppm of silicic acid as a nutrient (fertilizer) to a culture solution to allow the roots of rice plants to absorb it.

It has never been known hitherto, however, that pathogens can be killed by spraying an aqueous solution of an alkali metal silicate on the surface of leaves of various agricultural and horticultural plants.

PROBLEMS TO BE SOLVED BY THE INVENTION

In recent years, pesticide contamination on various agricultural and horticultural crops has become an issue, and recent studies has focused on a cultivation without using conventional chemical pesticides.

It is therefore an object of the present invention to provide a foliar spray agent containing an alkali metal silicate harmless to human and animals, as an active ingredient, for protecting agricultural and horticultural plants against disease injury and a method for protecting these plants against disease injury.

SUMMARY OF THE INVENTION

The present invention relates to:

(1) a foliar spray agent for protecting agricultural and horticultural plants against disease injury which comprises an alkali metal silicate as an active ingredient, and (2) a method for protecting agricultural and horticultural plants against disease injury which comprises spraying an aqueous solution comprising an alkali metal silicate as an active ingredient on the surface of leaves of the agricultural and horticultural plants.

The alkali metal silicates used in the present invention include $Na_2SiO_3$, $Na_4SiO_4$, $Na_2Si_2O_5$, $Na_2Si_4O_4$, $K_2SiO_3$, $KHSi_2O_5$, $K_2Si_4O_9 \cdot H_2O$ and the like, alone or in combinations thereof. Suitable examples are liquid potassium silicate from Nippon Liquid Fertilizer Co., Ltd. ($K_2O$ 6.0% $SiO_2$ 25%) and liquid sodium silicate from Nippon Soda Co., Ltd. (specific gravity 41.5, molar ratio 3.12, silicon dioxide 28.47, sodium oxide 9.42).

The foliar spray agent of the present invention is usually formulated as a concentrated stock solution and is appropriately diluted with water before use.

During formulation, conventional auxiliary agents such as stabilizers or spreader for achieving effective adhesion of the agent on foliar surfaces may be added, and other agricultural chemicals may also be incorporated in order to ensure the effect of the agent or to expand the application range of the agent of the invention.

The concentrated stock solution is diluted with water to contain approximately 0.006 mg ~ 0.025 mg/ml alkali metal silicate, and sprayed uniformly on entire foliar surfaces of plants.

The foliar spray agent of the present invention has been applied to various agricultural and horticultural plants such as, rice, potatoes, cucumbers, watermelons, tomatoes, strawberrys, pears, peaches, grapes and the like, and has proved to be remarkably effective in killing the pathogens, resulting in considerable increase in the crop yields.

EFFECT OF THE INVENTION

The foliar spray agent of the present invention showed an excellent protection of agricultural and horticultural plants from disease injury.

Since the active ingredient alkali metal silicate is a natural component with no harm to human and animals, it can be applied safely without any disadvantageous contamination as caused by conventional synthetic organic pesticides.

Consequently, it is expected that a great contribution will be made by the present invention to the agricultural and horticultural industry.

EXAMPLE

The following examples illustrate the present invention. All parts are by weight unless otherwise stated.

EXAMPLE 1

Preparation of foliar spray agent stock solution 60 parts of liquid potassium silicate (note 1), 35 parts of liquid sodium silicate (note 2), 0.5 parts of EDTA.Fe salt, 1 part of EDTA.Mg salt, 2 parts of citric acid and 100 parts of water were mixed uniformly to give a foliar spraying agent stock solution.

The stock solution can be diluted up to about 1000 times with water. The diluted solution can be sprayed on foliar surfaces of various agricultural and horticultural plants to protect them effectively against diseases. An increased crop yield can then be attained.

Note 1:
Nippon Liquid Fertilizer Co., Ltd., containing 6.0% $K_2O$ and 25% $SiO_2$.

Note 2:
Nippon Soda Co., Ltd., containing 9.4% Na and 28.47% $SiO_2$, and diluted 1:2000.

EXAMPLE 2

Protection test on rice from blast

A paddy field of 900 $m^2$ was divided into three plots, the first plot for treatment with no pesticide, the second plot with commercially available pesticides, and the third plot with the spray agent of the present invention. Rice seedlings were transplanted into each plot by conventional method. On day 50, 70 and 95 after transplantation, the pesticides were sprayed. The occurrence of spontaneous blast was determined on day 20 after each treatment on each plot (in June, July, August: three times). The blast occurrence (%) was calculated according to the following equation in order to evaluate the effectiveness of the pesticides.

$$\text{Blast occurrence (\%)} = \frac{A}{B} \times 100$$

A: the number of leaves showing apparent blast spots,
B: the total number of leaves tested.

The above described test was repeated 3 times, in 1987, 1988, and 1989, using the pesticides indicated.

In the plot for the spray agent of the present invention, the stock solution prepared in Example 1 was diluted 1:1000 with water and sprayed on foliar surfaces at 0.025 ml/m². In the plot for the commercially available pesticides, Fujiwan emulsion from Nippon Pesticide Co., Ltd. was diluted 1:100 with water and sprayed on foliar surfaces at 0.020 ml/m². For fertilization, conventional compound fertilizer was applied equally to each plot at 33 g/m² on May 5.

Results of this test are shown in Table 1.

TABLE 1

| Evaluation | Blast occurence (%) in each plot treated with the spray agent of: | | |
|---|---|---|---|
| | the present invention | commercially available pesticide | Control |
| June, 1987 | 5 | 5 | 10 |
| July, 1987 | 2 | 6 | 18 |
| August, 1987 | 0 | 10 | 22 |
| June, 1988 | 4 | 8 | 15 |
| July, 1988 | 3 | 16 | 22 |
| August, 1988 | 0 | 20 | 26 |
| June, 1989 | 6 | 9 | 17 |
| July, 1989 | 4 | 21 | 23 |
| August, 1990 | 0 | 20 | 28 |

EXAMPLE 3

Protection test on cherry tomato from disease injury 2,400 of cherry tomato seedlings were transplanted to 900 m² greenhouse. The stock solution prepared as in Example 1 was diluted 1:1000 with water and 4000 l of the diluted solution was sprayed on foliar surfaces of the cherry tomato seedlings on day 30 after transplantation. After the first treatment, the treatment was repeated every 10 days with increasing the amount of the agent with the growth of the cherry tomatoes. The seedlings were treated 12 times in total and the total amount of the diluted solution used reached 48,000 l. During the cultivation, Kuminhosuka (manufactured by Nissan Chemical Industrial Company) was applied to each plot as a basal fertilizer (40 kg N, 45 kg P and 40 kg K per 10 ares) on Mar. 20.

During this cultivation, no cherry tomato was infected with pathogens. The very good growth of the plants was observed and high quality tomatoes could be harvested until around Oct. 15th. The total yield amounted 20 tons.

In contrast, cherry tomatoes which were cultivated analogously but without the pesticide of the present invention were infected with the pathogens such as gray mold, downy mildew, powdery mildew and the like. The plant growth and fruit quality of them were distinctly inferior, and the harvesting period was shorter and the total yield was only 8 tons.

As evident from the above observation, commercially valuable cherry tomatoes can be obtained in high quality and in high yield using the agent of the present invention.

What is claimed is:

1. A method for protecting a plant against disease injury induced by a plant pathogen which comprises spraying the foliar surface of the plant with an aqueous solution consisting essentially of from about 0.006 mg/ml to about 0.025 mg/ml of an alkali metal silicate as the effective ingredient.

2. The method of claim 1 wherein the alkali metal silicate is a sodium or potassium alkali metal silicate or a combination thereof.

3. The method of claim 2 wherein the alkali metal silicate is selected from the group consisting of $Na_2SiO_3$, $Na_4SiO_4$, $Na_2Si_2O_5$, $Na_2Si_4O_4$, $K_2SiO_3$, $KHSi_2O_5$, $K_2Si_4O_2 \cdot H_2O$ or a combination thereof.

* * * * *

UNITED STATES PATENT AND TRADEMARK OFFICE
CERTIFICATE OF CORRECTION

PATENT NO. : 5,183,477
DATED : February 2, 1993
INVENTOR(S) : Toshio Masuda

It is certified that error appears in the above-indentified patent and that said Letters Patent is hereby corrected as shown below:

On the title page: Item [21]: The Application Serial Number is incorrectly printed as 102,011 and should read --602,991--.

Signed and Sealed this

First Day of March, 1994

Attest:

BRUCE LEHMAN

Attesting Officer     Commissioner of Patents and Trademarks